(12) United States Patent
Qvortrup

(10) Patent No.: US 12,005,031 B2
(45) Date of Patent: Jun. 11, 2024

(54) DEVICE FOR MONITORING THE MEDICATION OF A PATIENT

(71) Applicant: KIBODAN A/S, Rodovre (DK)

(72) Inventor: Klaus Qvortrup, Gentofte (DK)

(73) Assignee: K1BODAN A/S, Rodovre (DK)

( * ) Notice: Subject to any disclaimer, the term of this patent is extended or adjusted under 35 U.S.C. 154(b) by 136 days.

(21) Appl. No.: 17/436,043

(22) PCT Filed: Mar. 6, 2020

(86) PCT No.: PCT/EP2020/056043
§ 371 (c)(1),
(2) Date: Sep. 2, 2021

(87) PCT Pub. No.: WO2020/182667
PCT Pub. Date: Sep. 17, 2020

(65) Prior Publication Data
US 2022/0168187 A1 Jun. 2, 2022

(30) Foreign Application Priority Data
Mar. 8, 2019 (EP) ..................................... 19161625

(51) Int. Cl.
*A61J 7/04* (2006.01)
*A61J 1/03* (2023.01)
(Continued)

(52) U.S. Cl.
CPC .............. *A61J 7/0427* (2015.05); *A61J 1/03* (2013.01); *A61J 7/0084* (2013.01); *A61J 7/0481* (2013.01);
(Continued)

(58) Field of Classification Search
CPC ...... A61J 7/0427; A61J 7/0084; A61J 7/0481; A61J 1/03; A61J 2200/30; A61J 2200/70; G16H 20/13
See application file for complete search history.

(56) References Cited

U.S. PATENT DOCUMENTS 8,025,149 B2 * 9/2011 Sterry .................. A61J 7/0436
206/534
9,427,377 B1 * 8/2016 Miceli .................... G08B 21/24
(Continued)

FOREIGN PATENT DOCUMENTS

EP 2745827 6/2014
WO WO2017184055 10/2017

OTHER PUBLICATIONS

International Search Report on corresponding PCT application (PCT/EP2020/056043) from International Searching Authority (EPO) dated Apr. 3, 2020.
(Continued)

Primary Examiner — Michael Collins
(74) Attorney, Agent, or Firm — Shore 1P Group, PLLC; Howard J. Klein

(57) ABSTRACT

The device is adapted to accommodate medication for different days or for different times of a single day such as morning, midday and evening. A pill box with sections may be used for partitioning the medication. The pill box is contemplated to have at least one see-through wall or lid such that one may see medication or a label in the pill box. Pairs of light emitters and light receivers are used to detect medication and a processing unit for receiving output signals of the light receivers is used together with a communications module for transmitting a status signal of the pill box.

12 Claims, 2 Drawing Sheets

(51) Int. Cl.
*A61J 7/00* (2006.01)
*G16H 20/13* (2018.01)

(52) U.S. Cl.
CPC .......... *G16H 20/13* (2018.01); *A61J 2200/30* (2013.01); *A61J 2200/70* (2013.01)

(56) References Cited

U.S. PATENT DOCUMENTS

| | | | |
|---|---|---|---|
| 9,901,516 B2* | 2/2018 | Rodriguez | A61B 5/01 |
| 10,105,287 B2* | 10/2018 | Thomas | A61J 7/0418 |
| 2005/0107899 A1* | 5/2005 | Steffen | A61M 5/172 |
| | | | 700/231 |
| 2008/0059228 A1* | 3/2008 | Bossi | G16H 30/20 |
| | | | 705/2 |
| 2008/0277307 A1* | 11/2008 | Mazur | A61J 7/0481 |
| | | | 206/534 |
| 2009/0120042 A1* | 5/2009 | Zieher | B65B 35/06 |
| | | | 53/494 |
| 2009/0152291 A1* | 6/2009 | Ohmura | G07F 17/0092 |
| | | | 221/197 |
| 2012/0006708 A1* | 1/2012 | Mazur | A61J 7/0481 |
| | | | 206/438 |
| 2015/0283036 A1* | 10/2015 | Aggarwal | A61J 7/0436 |
| | | | 206/534 |
| 2015/0290084 A1 | 10/2015 | Kim | |
| 2018/0107976 A1* | 4/2018 | Sambrailo | G06Q 10/0833 |
| 2019/0269576 A1* | 9/2019 | Grosfils | G16H 20/13 |

OTHER PUBLICATIONS

Written Opinion on corresponding PCT application (PCT/EP2020/056043) from International Searching Authority (EPO) dated Apr. 3, 2020.

* cited by examiner

DEVICE FOR MONITORING THE MEDICATION OF A PATIENT

CROSS-REFERENCE TO RELATED APPLICATION

This application is the National Phase, under 35 U.S.C. § 371(c), of International Application No. PCT/EP2020/056043, filed Mar. 6, 2020, which claims priority from European Application No. EP 19161625.9, filed Mar. 8, 2019. The disclosures of all of the referenced applications are incorporated herein by reference in their entirety.

BACKGROUND

The invention concerns a device for monitoring the medication of a patient. In particular, the invention concerns a device which is compact, mobile and thereby user-friendly and enables automatic messaging to the user e.g. a patient or relative of the patient or a health care professional.

Pill boxes are typically used for the dosing of medication, in particular the medication of pills.

Conventionally, manufacturers have applied so-called matrix solutions, in which a pill box device is partitioned in a number of sections constituting compartments arranged in matrix form, meaning that the pill box is partitioned in normally two or more rows and two or more columns.

Such devices in matrix form are adapted to carry pill boxes corresponding to all days of the week, such as for instance the device under the trademark MediMax™.

WO 2017/184055 discloses a device having an electronic communication module, and a housing adapted to receive a matrix pill box in a releasable manner.

Sensor units are arranged so that each sensor unit is located under a section/individual compartment. The sensor unit detects the presence of the medicament in the section and includes a light source to light up the compartment and a detector for detecting reflected light.

US 2015/0283036 discloses also a matrix arrangement including a device with a replaceable tray and/or grid, in which the grid contains wells which may be filled by the user. In a particular embodiment, a separated column from the tray is placed in a device, such that it forms a one-column device to which a solid, non-transparent lid is adapted.

SUMMARY

It is an object of the present invention to be able to provide a device in which the pills are visible from the outside with or without a lid or closure.

It is also another object of the present invention to provide a device in which the labelling of different sections at the bottom or along a side of each section is visible from the outside. Alternatively, a single label may extend across several sections. The sections may be portioned by means of partition walls that are removable or do not extend all the way into contact with the bottom surface. In this way the label may slide underneath partition walls when placing the label in the pill box. Alternatively, the partition walls may be removed while placing the label in the pill box.

It is another object of the present invention to provide a device which is simple, compact, mobile and thereby user-friendly.

These and other objects are solved by the present invention.

Accordingly, there is provided a device for monitoring the medication of a patient, said device comprising:
a compartment including a compartment opening for accommodating a pill box, said pill box being partitioned in sections for storing medication corresponding to different times of the day, (said sections ranging in number from 1), each respective section intended to store medication having a bottom for supporting a label;
a closure for closing and opening said pill box such that said medication may be placed in a respective section and removed from a respective section, and without accidentally falling out while storing said medication;
said device further comprising
a paired light emitter and light receiver for each respective section of said pill box for detecting medication in each respective section intended to store medication, each of said respective light emitters being configured for emitting light substantially parallel with said bottom through each respective section, and each of said respective light receivers being configured to receive light emitted from said respective light emitters, and transmitted through each respective section;
said device further comprising
a processing unit for receiving respective output signals of said respective light receivers, and transmitting a status signal for each respective section of said pill box via a communications module to a monitor for presenting a storage status of said medicine being stored in each respective section of said pill box such that the medication of said patient may be monitored.

Thus, each section in the pill box corresponds to a certain time of the day, for instance breakfast, lunch, dinner and bedtime, so that the "whereabouts" of the pills in a given section of the pill box can be tracked (monitored) in a device which is much simpler and compact than any prior art device.

The compartment may be configured to accommodate a pill box for a day's medication, i.e. a pill box for a single day. Thus, the dimensions of the compartment may be congruent with the dimensions of a pill box for a single day. In this way there may not be room for two pill boxes (or more) to be placed in the compartment. This may for example ensure that days are not interchanged.

A section of the device is equipped with sensors in the form of a pair of light emitter and light receiver (detector), whereby the light being emitted by the light emitter of such pair, travels substantially parallel with said bottom, i.e. parallel with the plane defined by the surface of each bottom section. The sensor detects medications, or said in other words, if no medication is detected, it may be concluded that no medication is present.

The user, e.g. a patient, is benefited by higher safety and tranquility as he/she is not dependent on his/her memory for remembering taking a pill during the day and a message alert may only be sent where necessary.

The device is also able to remind health care personnel and/or relatives, via smartphone or PC, if the user has not taken the pill. This may be done, example by communicating with a server hosting a web page, which health care personnel and/or relatives may log on to, and follow the status of the device and the medication.

The design of the web page may vary, however in general it is contemplated that the design should include a visual indication or figure of the status of the respective sections, for example a green or red button depending whether or not the medication has been taken.

The user is also benefited by the device being little, light, as well as portable or mobile, so that it can be transported everywhere within the home or outside, e.g. during travel.

The sensors in the device may register automatically when the pills are being withdrawn from the device.

The medication may be a pill, a fluid, a créme, a liquid, a container for eye medication or other type of container for example a syringe also having a needle for injecting the contents of the container into the patient.

The sections preferably range in number from 1 to 4, corresponding to a breakfast section, lunch section, dinner section and bed time section.

The device according to the present invention reduces also the number of visits that healthcare personal need to comply with in order to ensure or control that the user has taken the pills. Also, for private persons, the device enables the relatives of the user to remember the taking of the pills, should this be forgotten.

In an embodiment of the invention, said pill box is detachable from the device.

This further promotes the user-friendliness of the device, as the pill box is thus removable and can be transported to e.g. a pharmacy or hospital for refilling with pills according to a given prescription, and particularly, it also enables the user to continue the use of already known devices in matrix form and adapted to carry pill boxes corresponding to all days of the week, such as for instance the device under the trademark MediMax™.

The user does not need to change known daily routines and learning new technology and simply continue using the device in matrix form such as MediMax™, as usual. In other words, no burden on learning new technologies or changing daily routines is imposed on the user.

In an embodiment of the invention, said closure is integral with said pill box.

The closure may thus be part of the pill box itself and acts as a lid.

Preferably the closure is adapted to slide in the length direction of the pill box so as to expose to the user a respective section intended to store medication. The closure may have ribs protruding from the surface of the closure such that it may be easier to grip/slide the closure on and off.

In a particular embodiment, the closure is divided in separate closure windows corresponding to each respective section whereby access to a particular section is obtained without opening for any of the other sections.

In another embodiment of the invention, the closure is transparent or constituted by a net or grid. This enhances the simplicity and use of the device, since the pills are visible from the outside with or without a lid or closure.

This also enables the use of labels on the bottom-surface of the device or the bottom of a section of the pill box for identification of e.g. the time of the day corresponding to the respective section, as well as quick identification of whether there are pills in box or not.

The labels may also contain information for the healthcare personal about what type of pill or medicament each section has or instructions concerning the particular medication.

In another embodiment of the invention, the device comprises a bottom-surface, e.g., a bottom plate, for placing said pill box on a horizontal surface during intended use of said device, such that said compartment opening faces upwards. The pill box may then easily and quickly be adapted into the device.

In an embodiment of the invention, each of said light emitters is configured for emitting light in a substantially horizontal plane during intended use of said device, for example when the device is arranged on a table.

In another embodiment of the invention, the device comprises an array of light emitters and an array of light detectors/receivers for each respective section of said pill box.

This enables better control of the pills within a given section of the pill box, for instance if a pill within a section moves to a different position, or where several types of pill are present in a section, e.g. a circular and a cylindrical pill.

The arrays of light detectors are preferably located in the bottom surface (bottom plate) of the device and are arranged along the length direction of the bottom surface. There may be four pairs of light emitters and detectors per section.

In another embodiment of the invention, the device has a wireless communications module being a radio transceiver for a wireless telecommunications network. In a particular embodiment, the wireless communications module comprises a SIM-card reader.

It may also make use of an Ethernet cable instead of a wireless solution.

In another embodiment of the invention, the device comprises an accelerometer for determining the orientation of said device. It is desirable that the orientation of the device is horizontal, so the provision of the accelerometer enables avoiding the device being accidentally placed in a tilted or vertical orientation (position).

In a particular embodiment, the processing unit is configured to receive an output signal of said accelerometer, and to provide an error signal when said device has a non-horizontal orientation.

In order to save battery power, the accelerometer and processing unit may be configured so that the processing unit detects or reacts to the rising edge of the output signal from the accelerometer.

A delay may be used such that the inclination of the rising edge is reduced in order to avoid that the processing unit misses a signal from the accelerometer—for example if the processing unit had been in a sleep state.

In another embodiment of the invention, the device comprises a filter for passing the frequency of the light emitted by said respective light emitters and for filtering daylight.

Hence, the sensor sends a signal to the processing unit but removes the frequencies which are not relevant for the measurement. This ensures also that the sensors are not sensitive to day light and thus the use of a transparent closure be possible.

Other wavelengths of light than the visible wavelengths may be used, for example infrared light.

In another embodiment of the invention, the device comprises a sensor for detecting when said pill box is in said compartment.

The sensor is preferably located in the bottom surface of the device and sends a signal or alarm to the user when e.g. the pill box has been forgotten to be adapted into the device.

In a particular embodiment, the processing unit is configured to receive an output signal of said sensor, and to provide an error signal when no device is detected.

The sensor may be a light sensor, which sends out light, and in case light is immediately reflected back due to the presence of the pill box (the bottom of the pill box) a signal is sent to the processing unit which identifies this as a presence of the pill box—in case no pill box is present, the device may alert this for example by the use of an LED which sends out a light signal.

In another embodiment of the invention, each of said respective status signals is indicative of said medication being in respective sections.

The device may also include a power supply in the form of batteries. This power supply is preferably arranged next to the processing unit.

Power to the device may also be provided in the form of plugging it into a wall plug—a transformer may then be included in order to transform the voltages from the net to the device.

In a general embodiment of the invention, the invention encompasses a device for monitoring the medication of a patient, said device comprising:
- a pill box being partitioned in sections for storing medication corresponding to different times of the day, said sections ranging in number from 1,
- each respective section intended to store medication having a bottom for supporting a label, and a closure for closing and opening said pill box such that said medication may be placed in a respective section and removed from a respective section, and without accidentally falling out while storing said medication,
- said device further comprising
- a paired light emitter and light receiver for each respective section of said pill box for detecting medication in each respective section intended to store medication,
- each of said respective light emitters being configured for emitting light substantially parallel with said bottom through each respective section,
- each of said respective light receivers being configured to receive light emitted from said respective light emitters, and transmitted through each respective section,
- said device further comprising
- a processing unit for receiving respective output signals of said respective light receivers, and transmitting a status signal for each respective section of said pill box via a communications module to a monitor for presenting a storage status of said medicine being stored in each respective section of said pill box such that the medication of said patient may be monitored.

BRIEF DESCRIPTION OF THE DRAWINGS

The invention will now be further described by the following figures of which.

DETAILED DESCRIPTION

Figure 1:
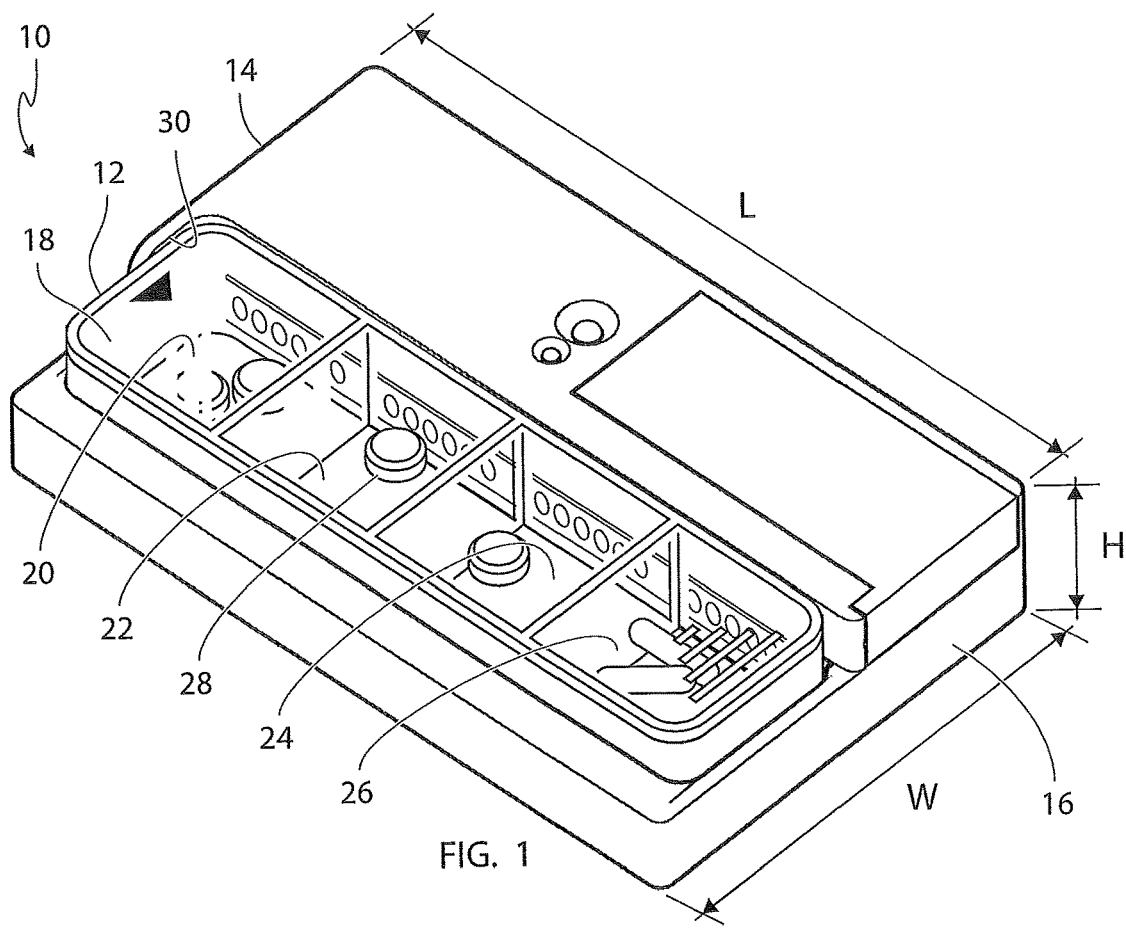
FIG. 1 is a is a perspective view of a device comprising a pill box.

The invention may, however, be embodied in different forms than depicted below, and should not be construed as limited to any examples set forth herein. Rather, any examples are provided so that the disclosure will be thorough and complete, and will fully convey the scope of the invention to those skilled in the art. Like reference numerals refer to like elements throughout. Like elements will, thus, not be described in detail with respect to the description of each figure.

FIG. 1 shows a device 10 according to the invention comprising pill box 12.

The device 10, here having dimensions L=145 mm, H=25 mm, W=85 mm, includes a first side wall 14 and a second side wall 16 opposite the first side wall 14.

The pill box 12 is provided with a closure 18 which is slidable along the length or horizontal direction "L" of the device 10.

The pill box 12 is partitioned in four sections 20, 22, 24, 26 for storing medication in the form of pills 28.

A label is provided in the pill box (not shown).

The closure 18 is transparent thus enabling to immediately visualize whether pills 28 are present in a given section and how many.

Closure 18 shows also a directional sign in the form of a triangle/arrow to indicate to the user in which direction to slide closure 18 when using the device 10—the pills are placed and removed from a respective section without accidentally falling out while storing the pills.

At a first end of the device there is provided a stop 30 that fixes the pill box 12 into place. The stop 30 may be integral with the first side wall 14 of the device 10.

The stop also ensures that the pill box is placed correctly into the device.

It is contemplated that the stop may include an overhang that extends over the closure at least in part so that the ribs of the closure prevent the pill box from being inserted into the device, because the ribs come into contact with the overhang.

This may also prevent the pill box from being inserted into the device with the sections in a wrong order, i.e. so that the processing unit thinks that the first section is night where it should have been morning for example.

The pill box may be an integral part of the device, i.e. so that it is not removable.

Figure 2:
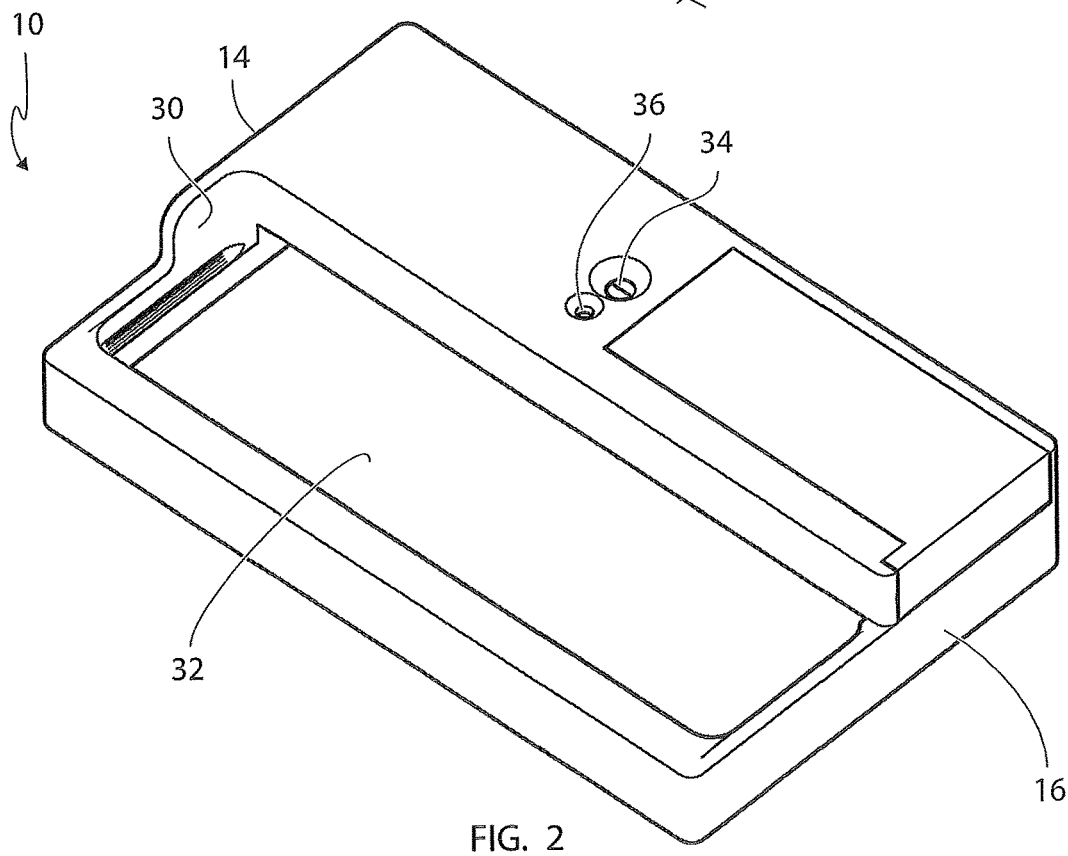
FIG. 2 is schematic drawing of the device without a pill box, showing the compartment into which a pill box is installed.

FIG. 2 is a perspective view from the top of the device 10 without the pill box 12, showing a compartment 32.

The compartment 32 has a hole/compartment opening facing upwards so as to receive the pill box 12.

Light-emitting diodes 34, 36 are arranged in the top flat (horizontal) face of the device 10. The light-emitting diode 34 provides a signal in the form of a red light when the pill box 12 is not present in the device 10, or the user e.g. patient has forgotten to take a pill due for a given time of the day, or if the device 10 is in a vertical orientation. Light-emitting diode 36 provides a signal when e.g. the battery of the device 10 is low.

The function of the LEDs may be exchangeable, and their sizes and amount of light output may also vary. In addition the device may have a loud speaker for outputting a sound signal such as an alarm when the battery is low or when it is time to take a medication or when a medication has been missed etc.

Figure 3:
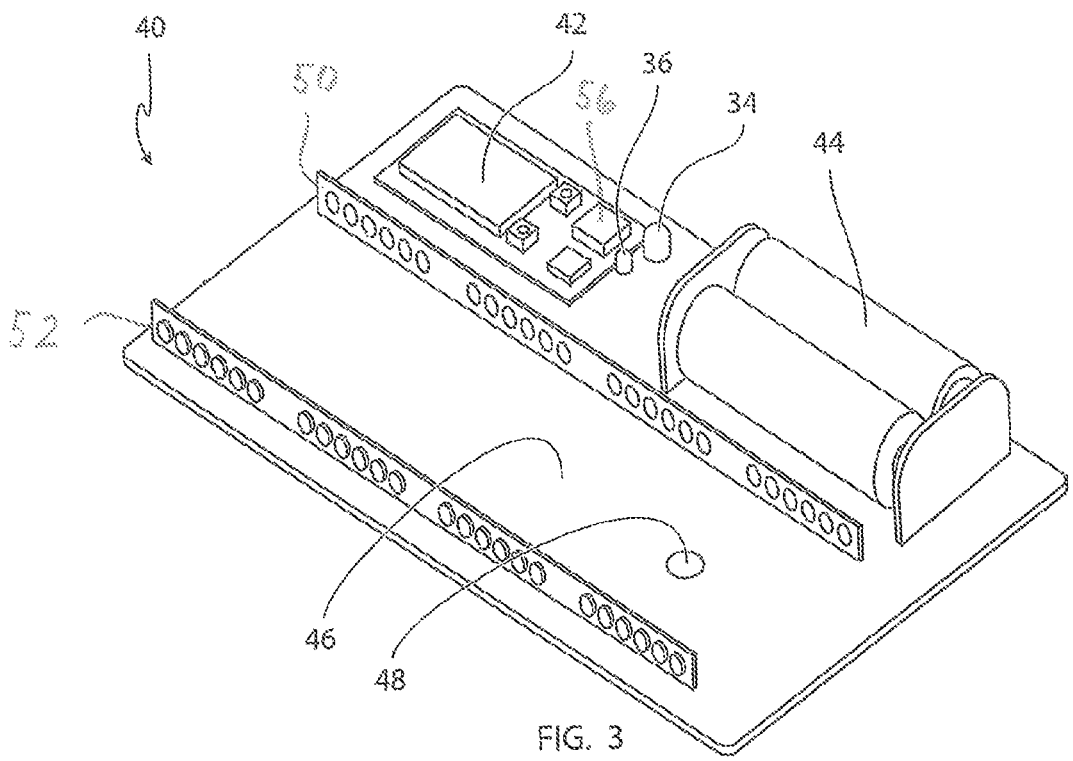
FIG. 3 is a perspective drawing of the bottom surface of the device showing the arrays of light emitters and light receivers.

FIG. 3 shows bottom surface 40 of the device 10. The bottom surface 40 includes a processing unit 42 and power supply in the form of batteries 44. The processing unit 42 may advantageously include or incorporate a wireless communications module, which may optionally include a SIM card reader.

Bottom surface 40 is adapted to accommodate the pill box (not shown), so that the pill box 12 is placed on a horizontal surface during intended use of said device.

The bottom surface 40 includes arrays of light emitters 50 (e.g., LEDs) and light detectors (light receivers) 52 as shown by the arrows. An array of light emitters and an array of light detectors is provided for each respective section of the pill box, in the figure illustrated as four sections. The section in the left correspond to the breakfast section 20, followed in the right direction by the lunch section, then the dinner section and lastly at the right the bed time section.

However, all of the LEDs 50 may be distributed at a substantially even distance between each other. If the emitters and receivers are arranged as integrated units, a reflector may be present on the opposite side.

The light emitters are configured for emitting light in a substantially horizontal plane 46 during intended use of said device 10. The light receivers 52 may advantageously be configured or operable with a filter that passes only light with the frequency of the light emitters 50, whereby daylight, for example, may be filtered out.

A sensor 48 which is connected to any of light diodes 34 36 is also provided in the bottom surface 40 to detect whether the pill box 12 is present or not.

The device 10 may advantageously include an accelerometer 56 configured for determining the orientation of the device. It is desirable for the device to be oriented horizontally; thus, the accelerometer enables avoiding the placement of the device in a tilted or vertical orientation. In a particular embodiment, the processing unit 42 is configured to receive an output signal of the accelerometer, and to provide an error signal when the device has a non-horizontal orientation.

Figure 4:
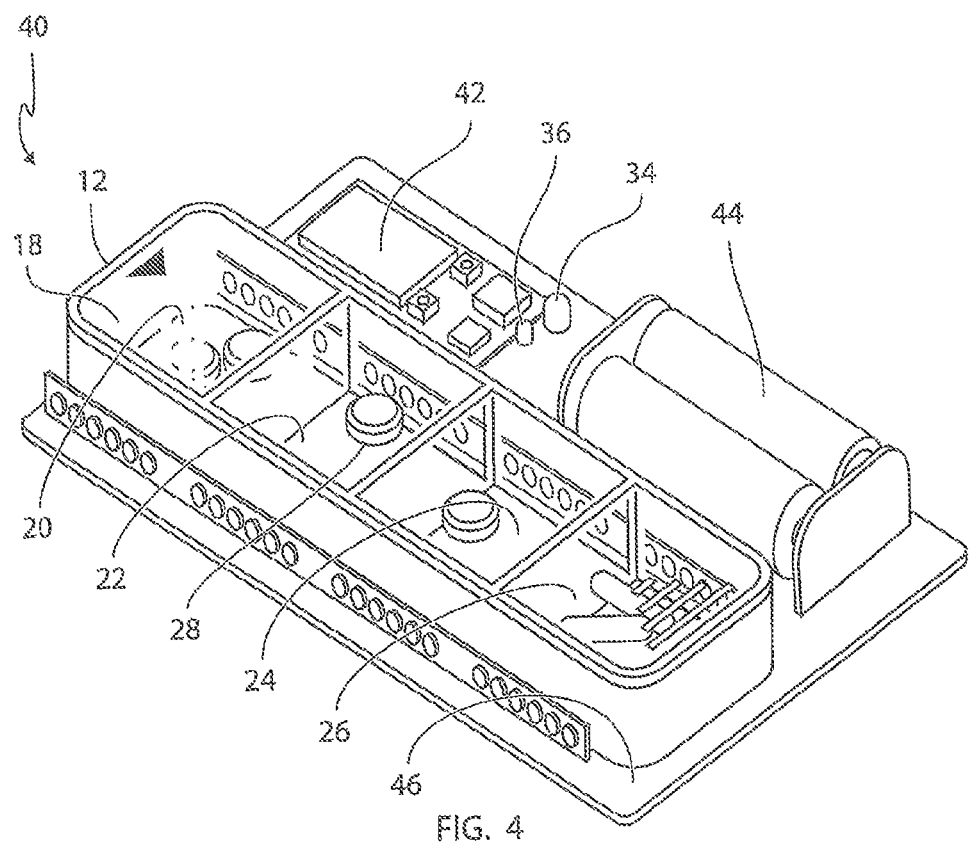
FIG. 4 shows the bottom surface (bottom plate) of FIG. 3 provided with a pill box.

FIG. 4 shows the bottom surface 40 of FIG. 3 with the pill box 12 adapted therein and corresponding sections 20, 22, 24, 26.

Ribs at the opposite end of the closure are provided to facilitate the sliding of the closure, i.e. the ribs constitute finger grips for contacting a finger such that it may be easier to remove/slide the closure.

Each respective section 20, 22, 24, 26 intended to store medication in the form of pills 28 has a bottom for supporting a label (not shown).

The invention claimed is:

1. A device for monitoring the medication of a patient, said device comprising:
    a compartment including a compartment opening configured for accommodating a pill box that is partitioned into a plurality of sections, each of the sections being configured for storing medication corresponding to a different time of day, each of the sections having a bottom;
    a closure for closing and opening the pill box such that medication may be placed in a respective section and removed from a respective section;
    a light emitter and a light receiver at the bottom of each respective section of the pill box for detecting medication in each respective section, each of the respective light emitters being configured for emitting light in a substantially horizontal plane parallel with the bottom of a respective section, and each of the respective light receivers being configured to receive light emitted from a respective light emitter and to emit an output signal that indicates the detection of the presence or absence of medication supported on the bottom of a respective section; and
    a processing unit configured for receiving the respective output signal of each of the respective light receivers, and for transmitting a status signal for each respective section of the pill box in response to the output signal of each of the respective light receivers, wherein each respective status signal is indicative of a storage status of medication stored in a respective section of the pill box.

2. The device according to claim 1, further comprising a bottom surface configured for placing the pill box on a horizontal surface during intended use of the device, such that the compartment opening faces upwards.

3. The device according to claim 1, further comprising an array of light emitters and an array of light detectors for each respective section of the pill box.

4. The device according to claim 1, further comprising a wireless communications module configured for communicating via a wireless telecommunications network.

5. The device according to claim 4, further comprising a SIM-card reader.

6. The device according to claim 1, further comprising an accelerometer configured for determining the orientation of said device.

7. The device according to claim 6, wherein the processing unit is further configured to receive an output signal of the accelerometer, and to provide an error signal when the device has a non-horizontal orientation.

8. The device according to claim 1, further comprising a filter configured for passing light of a frequency of the light emitted by the respective light emitters, and for filtering daylight.

9. The device according to claim 1, further comprising a sensor configured for detecting when the pill box is in the compartment.

10. The device according to claim 9, wherein the processing unit is further configured to receive an output signal of the sensor, and to provide an error signal when no pill box is detected.

11. The device according to claim 1, wherein each of the respective status signals is indicative of medication being in each of the respective sections.

12. A device for monitoring the medication of a patient, the device comprising:
    a pill box partitioned into a plurality of sections, each of the sections being configured for storing medication corresponding to a different time of day, each of the sections having a bottom, the pill box having a closure for closing and opening the pill box such that medication may be placed in each respective section and removed from each respective section;
    a light emitter and a light receiver in each respective section of the pill box and configured for detecting medication in each respective section, each of the respective light emitters being configured for emitting light in a substantially horizontal plane substantially parallel with the bottom of a respective section, each of the respective light receivers being configured to receive light emitted from one of the respective light emitters, each of the respective light receivers being operable to produce an output signal that indicates the detection of the presence or absence of medication supported on a bottom of a respective section; and
    a processing unit configured for receiving respective output signals of each of the respective light receivers, and for transmitting a status signal for each respective section of the pill box in response to each of the output signals, each of the status signals being indicative of a storage status of medication stored in a respective section of the pill box.

\* \* \* \* \*

UNITED STATES PATENT AND TRADEMARK OFFICE
CERTIFICATE OF CORRECTION

| | | |
|---|---|---|
| PATENT NO. | : 12,005,031 B2 | Page 1 of 1 |
| APPLICATION NO. | : 17/436043 | |
| DATED | : June 11, 2024 | |
| INVENTOR(S) | : Klaus Qvortrup | |

It is certified that error appears in the above-identified patent and that said Letters Patent is hereby corrected as shown below:

On the Title Page

Item [73] should read:
--KIBODAN A/S, Rodovre, DK--

Signed and Sealed this
Twenty-ninth Day of October, 2024

*Katherine Kelly Vidal*

Katherine Kelly Vidal
*Director of the United States Patent and Trademark Office*